(12) United States Patent
Adler et al.

(10) Patent No.: US 6,812,461 B1
(45) Date of Patent: Nov. 2, 2004

(54) PHOTOCATHODE SOURCE FOR E-BEAM INSPECTION OR REVIEW

(75) Inventors: David L. Adler, San Jose, CA (US); Marian Mankos, San Francisco, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 51 days.

(21) Appl. No.: 10/290,014

(22) Filed: Nov. 7, 2002

(51) Int. Cl.[7] .......................... H01J 37/73; G01R 31/28
(52) U.S. Cl. ......................................................... 250/310
(58) Field of Search ................................. 250/310, 311, 250/492.2, 306, 307

(56) References Cited

U.S. PATENT DOCUMENTS

| | | | |
|---|---|---|---|
| 4,820,927 A | * 4/1989 | Langner et al. | 250/492.2 |
| 4,877,326 A | 10/1989 | Chadwick et al. | |
| 4,970,392 A | * 11/1990 | Oettinger et al. | 250/423 P |
| 5,041,724 A | * 8/1991 | Feuerbaum et al. | 250/307 |
| 5,973,323 A | 10/1999 | Adler et al. | |
| 6,038,018 A | * 3/2000 | Yamazaki et al. | 356/237.1 |

OTHER PUBLICATIONS

Michelato et al., "Optical Properties of Cesium Telluride" Proc. of EPAC 200, Paris France, pp 8110–1812.*
Trotz, S., et al. "High Power Operation of a 17 GHz Photocathode RF Gun", Advanced Accelerator Concepts, edited by S. Chattopadhyay, 1997.
J.E. Clendenin, et al. "Reduction of Thermal Emittance of RF Guns", SLAC–PUB–8284, Oct. 1999.

* cited by examiner

*Primary Examiner*—John R. Lee
*Assistant Examiner*—James J. Leybourne
(74) *Attorney, Agent, or Firm*—Okamoto & Benedticto LLP

(57) ABSTRACT

One embodiment disclosed is an electron beam apparatus for examination of a specimen. The apparatus includes a photocathode source, an objective lens, a beam separator, and a projection lens. The photocathode source generates a primary electron beam with reduced energy spread. The low energy spread beam is focused onto the specimen by the objective lens. The beam separator separates a scattered electron beam from the primary electron beam, and the projection lens images the scattered electron beam. Software routines may analyze the image data for purposes of automated inspection or review.

19 Claims, 7 Drawing Sheets

PHOTOCATHODE SOURCE FOR E-BEAM INSPECTION OR REVIEW

BACKGROUND OF THE INVENTION

1. Field of the Invention

The present invention relates generally to specimen inspection and review. More particularly, the present invention relates to e-beam inspection and systems.

2. Description of the Background Art

Automated inspection and review systems are important in process control and yield management for the semiconductor and related microelectronics industries.

An example of an electron beam (e-beam) tool for an inspection or review system is shown in FIG. 1 for purposes of background explanation. The secondary electron emission microscope (SEEM) apparatus of FIG. 1 is a projection type system, where a large spot of electrons rather than a small one is formed at the surface of the specimen, and the secondary electrons from this spot are imaged onto a two-dimensional detector. Typically, the specimen may comprise a semiconductor wafer having integrated circuit related structures formed on its surface. Alternatively, the specimen may be another type of sample.

The system of FIG. 1 is described in U.S. Pat. No. 5,973,323, entitled "Apparatus and Method for Secondary Electron Emission Microscope," inventors Adler et al., and assigned at issuance to KLA-Tencor Corporation of San Jose, Calif. The disclosure of U.S. Pat. No. 5,973,323 is hereby incorporated by reference. As described in that patent, FIG. 1 shows the basic configuration for the Secondary Electron Emission Microscopy (SEEM) apparatus. An electron gun source 10 emits a beam 11 of primary electrons $e_1$ along path 12. The electron beam 11 is collimated by electron lens 13 and continues along path 12. Magnetic beam separator 14 then bends the collimated electron beam 11 to be incident along electron optical axis OA normal to the surface to be inspected. Objective electron lens 15 focuses the primary electrons, $e_1$, into a beam having a spot size typically in the range 1–10 mm and an incident energy on the order of 1 keV on specimen 9.

Primary electrons $e_1$ incident on the specimen 9 produce secondary electrons $e_2$ which travel back along the axis OA perpendicular to the inspection surface to objective electron lens 15, where they are re-collimated. Magnetic beam separator 14 bends the electrons to travel along image path 16. The electron beam along image path 16 is focused by projection electron lens 17 to image plane 18, where there is an electron detector 19, which is a camera or preferably a time delay integrating (TDI) electron detector. The operation of an analogous TDI optical detector is disclosed in U.S. Pat. No. 4,877,326, entitled "Method and Apparatus for Optical Inspection of Substrates," inventors Chadwick et al., and assigned at issuance to KLA Instruments Corporation. The disclosure of U.S. Pat. No. 4,877,326 is incorporated herein by reference. The image information may be processed directly from a 'back thin' TDI electron detector 19, or the electron beam may be converted into a light beam and detected with an optional optical system 20 and a TDI optical detector.

Despite advances in e-beam inspection and review, such as SEEM described above, further improvement may be made. For example, it is typically desirable to increase the resolution of an inspection or review system. Resolution may be defined as the smallest distance apart that two point may be distinguishable as separate points. Current e-beam inspection and review systems have resolutions of about 100 nanometers (0.1 micrometers). Generally, the higher the resolution, the smaller the defects that may be detected and characterized by the automated inspection and review systems. In other words, the resolution of an e-beam system limits the smallness of the features that may be detected and characterized. Hence, in order to detect and characterize smaller and smaller features on semiconductors and other specimens, it is desirable to increase the achievable resolution of the system.

SUMMARY

The present invention provides an apparatus, method and system for electron beam inspection of a specimen with improved resolution. One embodiment of the invention is an electron beam apparatus for examination of a specimen. The apparatus includes a photocathode source, an objective lens, a beam separator, and a projection lens. The photocathode source generates a primary electron beam with reduced energy spread. The low energy spread beam is focused onto the specimen by the objective lens. The beam separator separates a scattered electron beam from the primary electron beam, and the projection lens images the scattered electron beam. Software routines may analyze the image data for purposes of automated inspection or review.

DETAILED DESCRIPTION

The present invention uses a photocathode source to increase the achievable resolution of e-beam inspection systems. One embodiment of the present invention improves the potential resolution of an SEEM system. The photocathode source replaces previously used thermionic and field emission electron guns.

Figure 1:
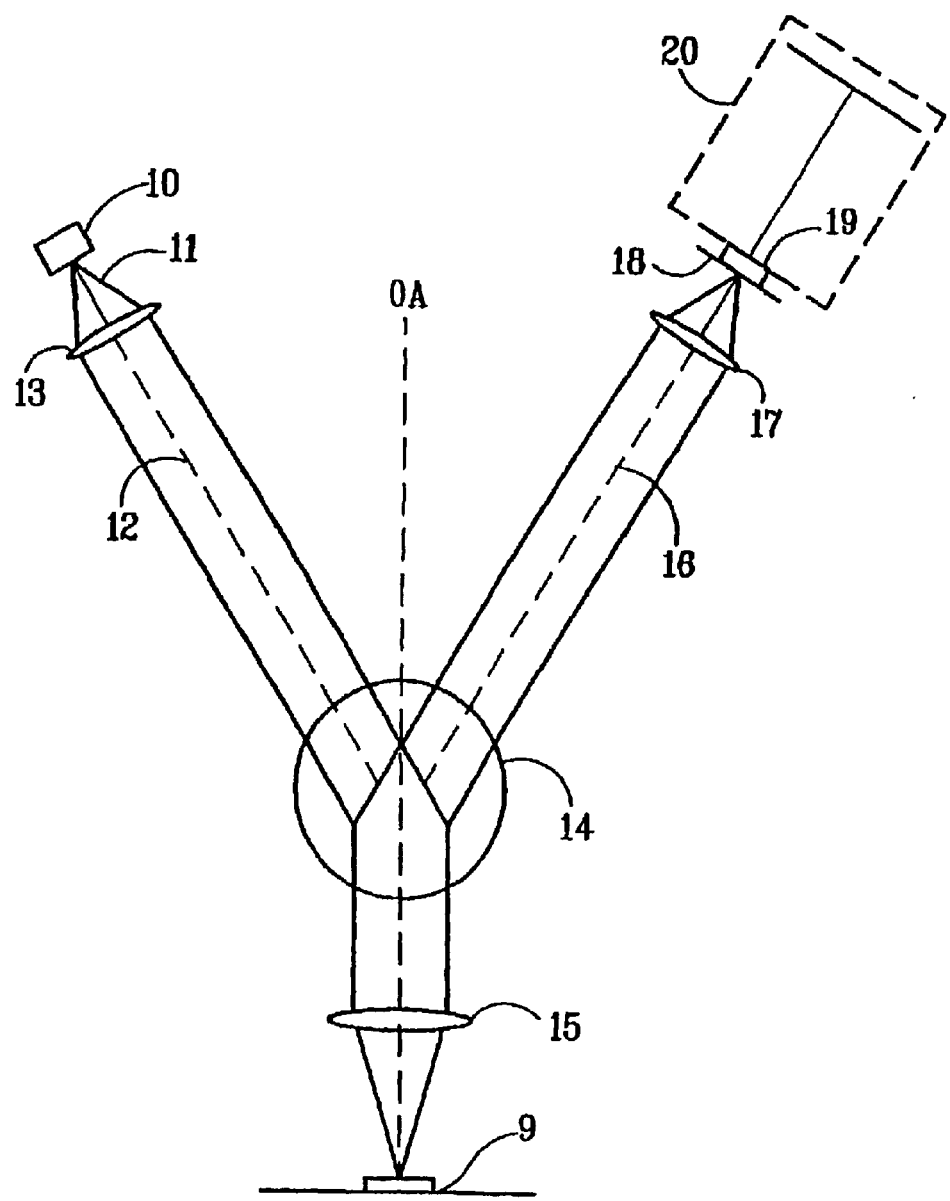
FIG. 1 shows the basic configuration for the Secondary Electron Emission Microscopy apparatus.
Figure 2:
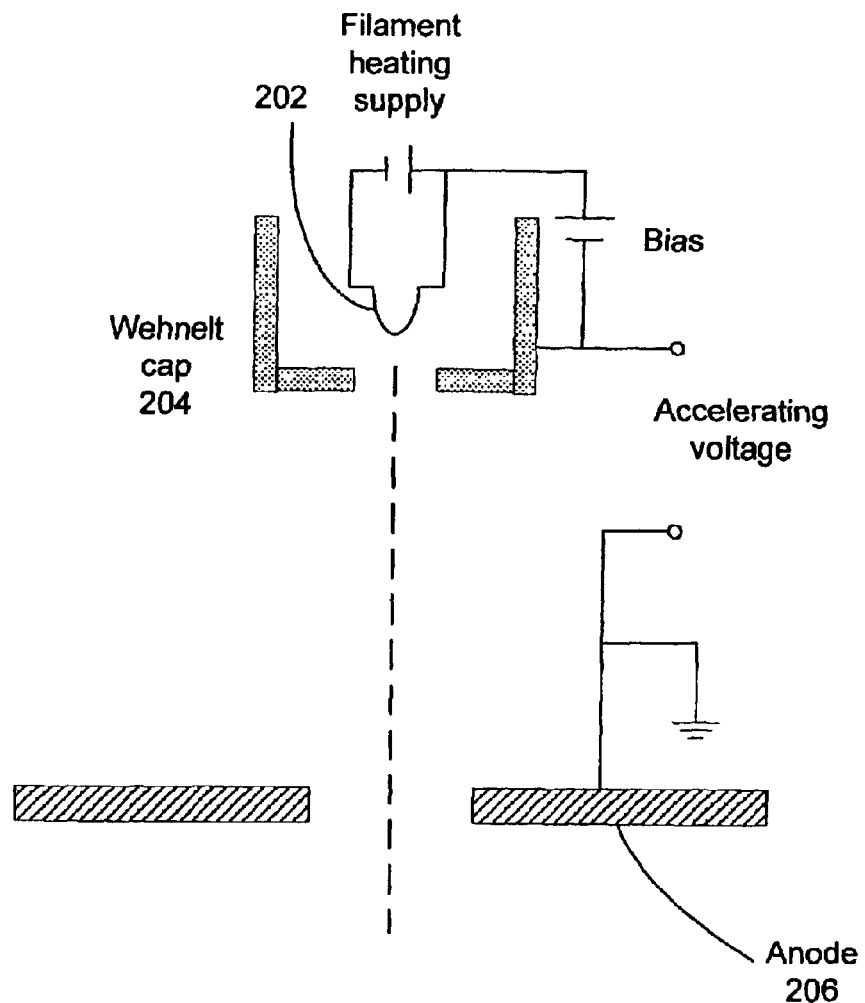
FIG. 2 is a simplified illustration of a conventional thermionic source for use in an e-beam system.

FIG. 2 is a simplified illustration of a conventional thermionic source 200 for use in an e-beam system. A thermionic source 200 includes a cathode 202 that is heated such that electrons are emitted from the cathode surface. Typically, thermionic sources use a tungsten hairpin filament or a lanthanum hexaboride (LaB6) crystal tip as the cathode 202. Thermionic emission is based on heating the cathode 202 to increase the number of electrons occupying energy levels above the Fermi energy. Some of these electrons will have enough energy to escape from the cathode material 202 and become free electrons. A Wehnelt cap 204 is typically used to house the cathode. A negative potential (relative to the cathode) is applied to the Wehnelt cap 204 such that a collection of electrons (space charge) forms in the space between the filament 202 and the cap 204. Electrons exit the space charge though a small opening in the Wehnelt cap 204. An anode 206 is held at a high positive voltage with respect to the cathode. The anode 206 may be in the form of an anode plate with an opening in it. The positive voltage accelerates the electrons towards the anode 206. The momentum of some of the electrons carries them through the opening in the anode 206 and down the column towards the specimen.

Disadvantageously, thermionic sources 200 result in an electron beam with a relatively large energy spread. The energy spread of electrons exiting a thermionic electron gun is typically over one electron volt. This relatively large energy spread limits the resolution achievable by e-beam systems that use thermionic sources 200.

Figure 3:
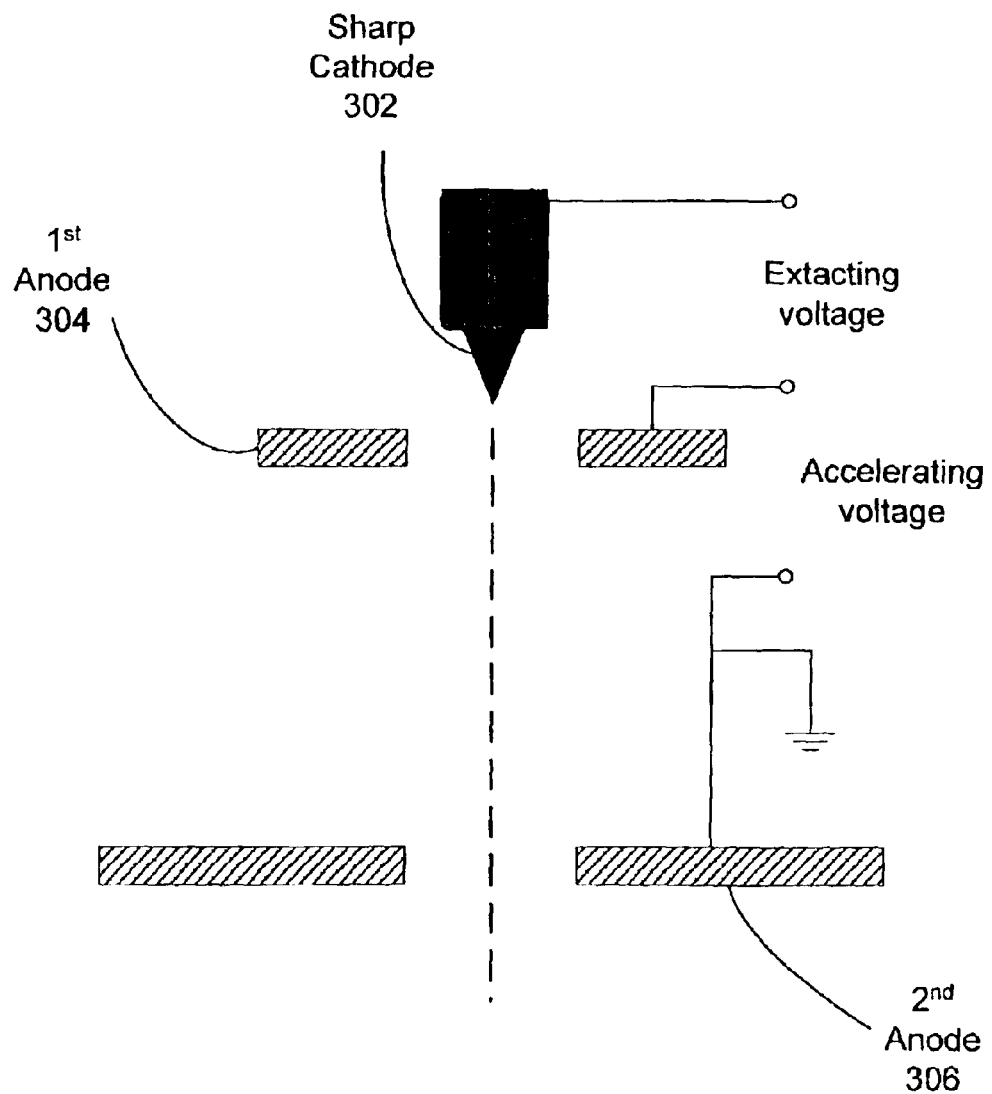
FIG. 3 is a simplified illustration of a conventional field emission source for use in an e-beam system.

FIG. 3 is a simplified illustration of a conventional field emission source 300 for use in an e-beam system. A typical field emission source 300 includes a cathode 302 shaped to have a sharp point. The cathode 302 may be, for example, a tungsten crystal. An extraction field (typically, a few kilovolts) is applied via a first anode 304, and very high electric fields are formed at the sharp tip 302. These high fields extract electrons from the tip 302 by way of a tunneling mechanism. A second anode 306 is held at a high positive voltage with respect to the cathode 302. The positive voltage accelerates the electrons towards the anode 306, and the momentum of some of the electrons carries them through the opening in the anode 306 and down the column towards the specimen. Field emission sources 300 require operate in higher vacuum and lower temperatures than thermionic sources 200. The lower temperature of operation of field emission sources 300 generally results in lower energy spreads than thermionic sources 200. For Shottky type field emission sources 300, a broader tip 302 is used which has a surface layer that enhances the emission of electrons from the cathode 302. The surface layer, for example, may comprise a layer of zirconia on the surface of the tungsten.

Figure 4:
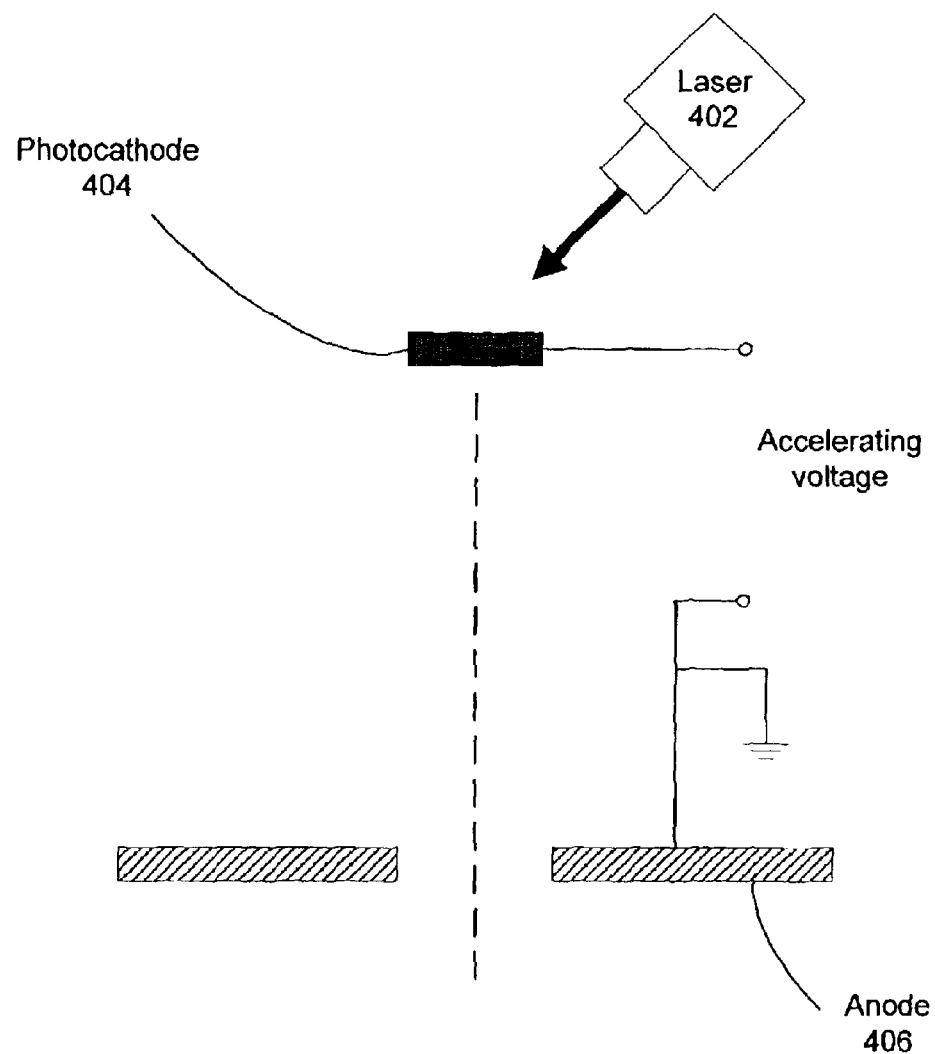
FIG. 4 illustrates basic components of a photocathode source for use in an e-beam system in accordance with an embodiment of the invention.

FIG. 4 illustrates basic components of a photocathode source 400 for use in an e-beam system in accordance with an embodiment of the invention. Photocathode sources 400 have not previously been used in e-beam inspection or review systems. In accordance with one embodiment, the basic components of the photocathode source 400 include a laser 402, a photocathode 404, and an anode 406. While certain components are illustrated in FIG. 4 for purposes of discussion, other embodiments of a photocathode source 400 may include other components varying from or adding to those illustrated.

The photocathode (or photosensitive cathode) 404 emits electrons in response to exposure to electromagnetic radiation. The photocathode 404 may comprise a semiconductor material. For example, the photocathode 404 may comprise Cesium Telluride or Gallium Arsenide. In a semiconductor with an energy bandgap of $E_{BG}$, a photon with an energy greater than the bandgap may be absorbed, resulting in the excitation of an electron from near the top of the valence band into the conduction band. The excited electron loses energy by electron-phonon scattering as it diffuses to the surface. In one embodiment, the photocathode material may comprise a negative electron affinity (NEA) emitter in that the vacuum level at the surface is below the conduction band minimum in the bulk material. Such an NEA emitter may include p-doping of the bulk material and/or a surface layer of an alkali metal to reduce the electron affinity.

The laser 402 should provide an output with a photon energy sufficiently high to excite electrons across the bandgap of semiconductor photocathodes 404. The laser 402 may output light, for example, in the ultraviolet wavelength range. Alternatively, for some photocathodes 404, the laser may output light in the visible wavelength range. The anode 406 is provided to accelerate the electrons emitted from the photocathode 404. The accelerated electrons may travel through an opening in the anode 406 and though a column to the specimen.

Figure 5:
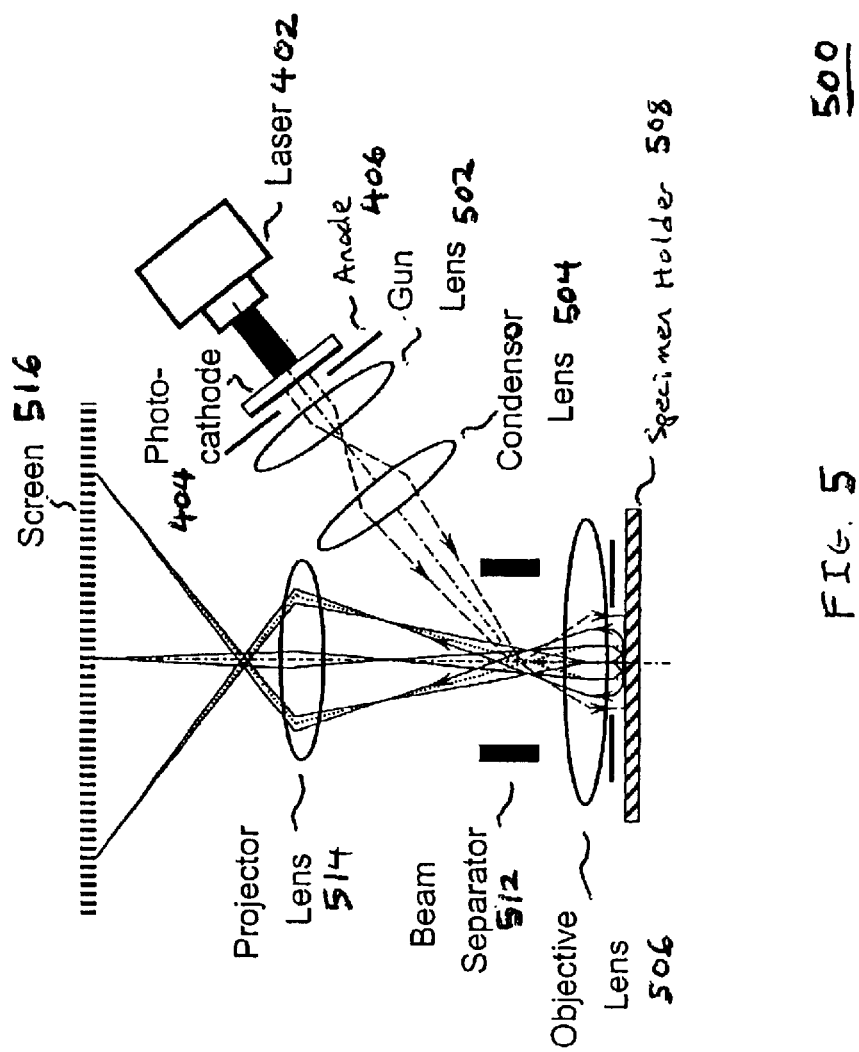
FIG. 5 illustrates an electron beam apparatus for review or inspection in accordance with an embodiment of the invention.

FIG. 5 illustrates an electron beam apparatus 500 for examining a specimen in accordance with an embodiment of the invention. In a preferred embodiment, the apparatus 500 may be an e-beam inspection or review apparatus for inpection or review of semiconductor substrates. The apparatus 500 as depicted includes a photocathode source 400, a gun lens 502, a condensor lens 504, an objective lens 506 which includes an extraction electrode 510, a specimen holder 508, a beam separator 512, a projector lens 514, and a screen 516. While certain components are illustrated in FIG. 5 for purposes of discussion, alternate embodiments of an electron beam apparatus in accordance with the invention may include other components varying from or adding to those illustrated.

An embodiment of the photocathode source 400 may include a laser 402, photocathode 404, and anode 406. The operation of such a source 400 is described above in relation to FIG. 4. The electron beam emitted by the photocathode source 400 may travel through a lens system that includes a gun lens 502 and a condensor lens 504. The gun lens 502 may comprise, for example, an electrostatic lens that forms a first crossover of the beam. The condensor lens 504 may comprise, for example, a magnetic lens that forms a second crossover.

The electron beam is focused onto the specimen by the objective lens 506. The specimen may be set on a specimen holder 508. When the specimen is biased slightly negative with respect to the cathode, the electrons are reflected and scattered above the surface. This imaging mode is called mirror electron microscopy. The scattered electrons are focused by the objective lens 506 to form a image of the specimen surface. A beam separator 512 is utilized to separate the scattered electron beam (the beam coming from the specimen) apart from the primary electron beam (the beam coming from the photocathode source 400). In one embodiment, the beam separator 512 may comprise a Wien filter that separates the two beams based on their velocities. Alternatively, the beam separator 512 may comprise a bending magnet configured to separate the beams. The projector lens 514 images the beam onto the screen or detector 516. The image formed on the screen or detector 516 is that of the specimen surface. The image may be viewed by a user or electronically processed and analyzed by the inspection or review system.

An electron inspection or review apparatus 500 with a photocathode source 400 is advantageous in that an electron beam with greatly reduced energy spread is achievable. Electron beams with a low energy spread of 100 meV (0.1 eV) to 50 meV (0.05 eV) or lower are attainable in such a system. In contrast, existing cathodes in inspection and review systems typically have an energy spread of 200 meV (0.2 eV) or more. This large energy spread from existing cathodes produces chromatic aberrations in the image and are a major source of blur in the image. One meV (milli-eV) is equal to one thousandth of an eV (electron volt).

With the reduced energy spread attainable with an inspection or review system 500 utilizing a photocathode source 400, a significantly improved resolution may be obtained in the electron images. Inspection and review systems using a photocathode source 400 can achieve resolutions in the range of 10 nm. Without the present invention, existing inspection and review systems would not be able to achieve resolutions below about 50 nm due to the chromatic aberrations.

Figure 6:
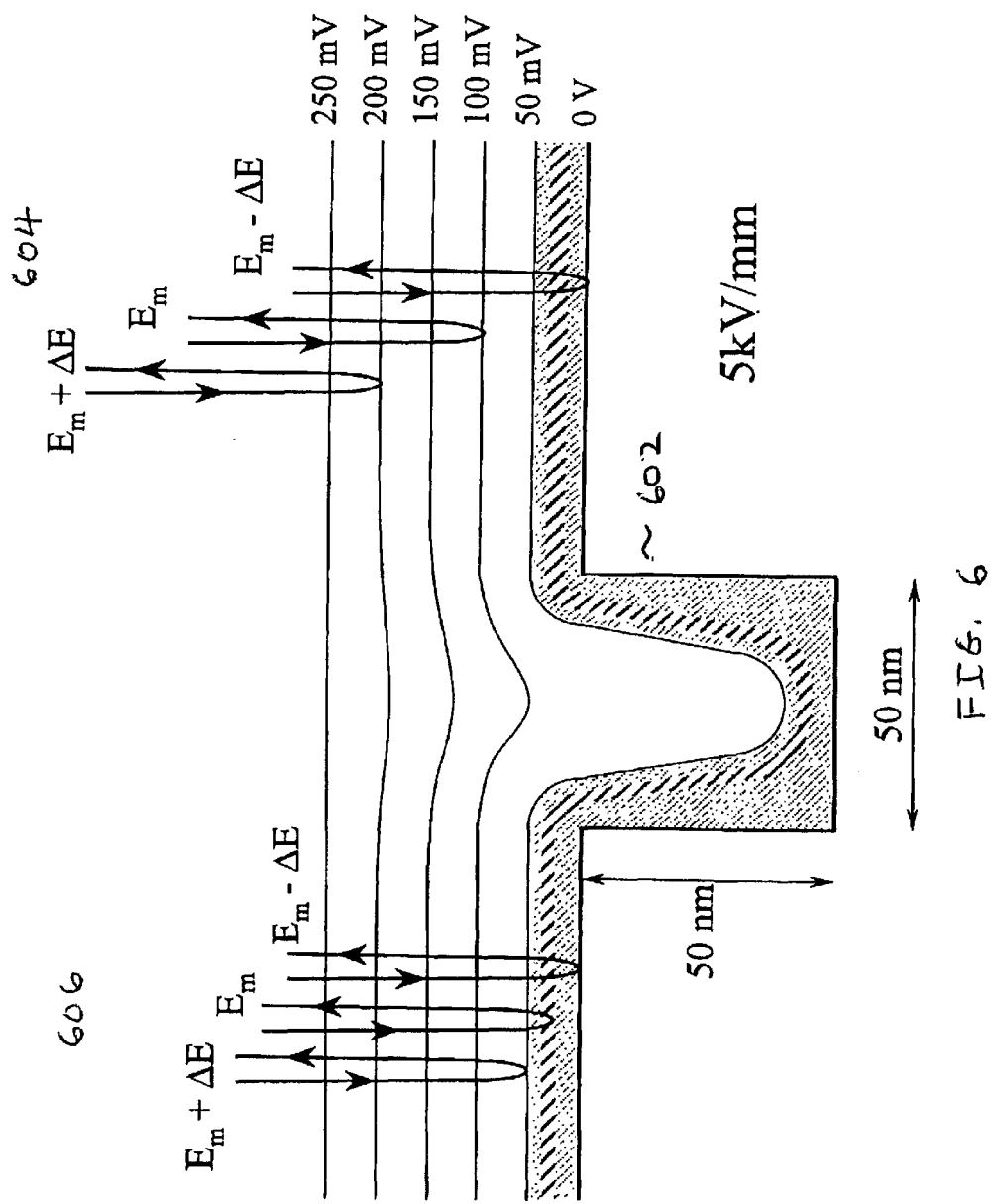
FIG. 6 is a diagram illustrating the relation between lower energy spread and improved resolution in accordance with an embodiment of the invention.

FIG. 6 is a diagram illustrating the relation between lower energy spread and improved resolution in accordance with an embodiment of the invention. A specimen feature 602 that is 50 nm in dimension is depicted for purposes of illustration. The diagram shows lines that represent equipotential voltage levels at 250 mV, 200 mV, 150 mV, 100 mV, 50 mV, and 0 mV across the surface of the specimen. Also depicted are illustrative electron paths for a conventional beam 604 with an energy spread of 200 meV and for a second beam 606 with a reduced energy spread of about 50 meV in accordance with an embodiment of the invention. As illustrated in FIG. 6, the larger energy spread of the conventional beam 604 causes a correspondingly large spread of the electrons as they impinge upon the surface of the specimen. As a result, features as small as 50 nm become difficult to resolve. In contrast, the narrower energy spread of the second beam 606 causes a correspondingly small spread of the electrons as they impinge upon the surface of the specimen. This enables features with dimensions of 50 nm or even less to be resolved.

Figure 7:
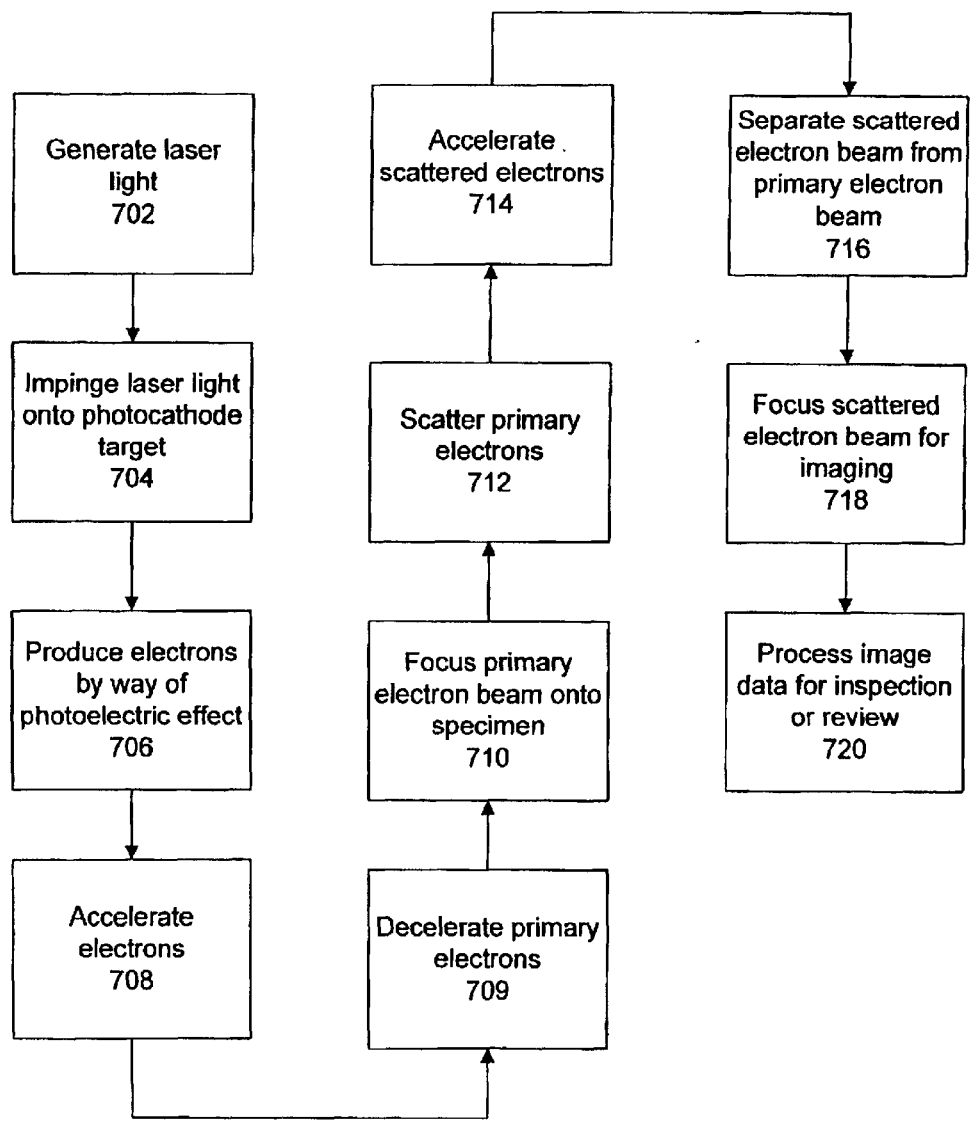
FIG. 7 is a flow chart depicting a method for e-beam examination of a specimen in accordance with an embodiment of the invention.

FIG. 7 is a flow chart depicting a method for e-beam examination of a specimen in accordance with an embodiment of the invention. The method 700 as depicted includes ten steps (702, 704, 706, 708, 710, 712, 714, 716, 718, and 720).

In the first step 702, coherent light is generated by a laser 402. In the second step, the coherent light Is impinged upon a photocathode target 404. As described above, the light may be in the ultraviolet or visible wavelength ranges. For semiconductor targets, the photon energy of the light should exceed the relevant energy bandgap of the semiconductor. As a result, in the third step 706, electrons are produced by way of the photoelectric effect. These electrons are then accelerated in the fourth step 708 (for example, by way of an anode 406) to form the primary electron beam. Various lenses, for example, gun lens 502, condensor lens 504, and objective lens 506, may operate on the primary beam. In the fifth step 710, the objective lens 506 and extraction electrode 510 decelerate and focus the primary electron beam onto an area of the specimen.

In the sixth step 712, scattered or secondary electrons are produced from the electron-illuminated area of the specimen. These electrons are then accelerated in the seventh step 714 by utilization of an extraction electrode 510. In the eight step 716, the scattered electron beam and the primary electron beam are separated using a beam separator 512. In the ninth step 718, the scattered electron beam is focused by the projector lens 514 to form an image of the area on a screen or detector 516. In accordance with embodiments of the invention, in the tenth step 720, software routines may operate upon the image data for purposes of automated inspection of a specimen or automated review and analysis of specimen defects.

The above-described diagrams are not necessarily to scale and are intended be illustrative and not limiting to a particular implementation. The above-described invention may be used in an automatic inspection or review system and applied to the inspection or review of wafers, X-ray masks and similar substrates in a production environment. While it is expected that the predominant use of the invention will be for the inspection or review of wafers, optical masks, X-ray masks, electron-beam-proximity masks and stencil masks, the techniques disclosed here may be applicable to the high speed electron beam imaging of any material (including perhaps biological samples).

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An electron beam apparatus for inspection or review of a specimen, the apparatus comprising:
    a photocathode source without electrical heating for generating a primary electron beam with energy spread of less than 100 meV;
    a objective lens for focusing the primary electron beam onto the specimen;
    a beam separator for separating a scattered electron beam from the primary electron beam; and
    a projection lens for imaging the scattered electron beam such that features with dimensions of less than 50 nm are resolvable.

2. The apparatus of claim 1, wherein the photocathode source includes a laser light source generating light that impinges upon a photocathode target.

3. The apparatus of claim 2, wherein the photocathode target comprises a semiconductor material with an energy bandgap.

4. The apparatus of claim 3, wherein the semiconductor material of the photocathode target comprises cesium telluride.

5. The apparatus of claim 3, wherein the semiconductor material of the photocathode target comprises gallium arsenide.

6. The apparatus of claim 3, wherein the laser light source produces a wavelength of light having a photon energy greater than the energy bandgap.

7. The apparatus of claim 6, wherein the wavelength of light is in a range of ultraviolet light.

8. The apparatus of claim 6, wherein the wavelength of light is in a range of visible light.

9. The apparatus of claim 1, wherein the apparatus comprises an electron beam inspection system and further comprises software routines for automated inspection of semiconductor specimens.

10. The apparatus of claim 1, wherein the apparatus comprises an electron beam review system and further comprises software routines for automated review and analysis of specimen defects.

11. A method for e-beam inspection or review of a specimen, the method comprising:

generating a primary electron beam using a photocathode source without electrical heating such that the primary electron beam has a low energy spread;

focusing the primary electron beam onto an area of the specimen;

separating a scattered electron beam from the primary electron beam; and imaging the scattered electron beam to produce an image of the area wherein features with dimensions of less than 50 nm are resolved.

12. The method of claim 11, wherein generating the primary electron beam comprises generating coherent light and impinging the coherent light upon a photocathode target.

13. The method of claim 12, wherein the coherent light comprises a photon energy greater than an energy bandgap of the photocathode target.

14. The method of claim 13, wherein the photocathode target comprises a semiconductor material.

15. The method of claim 14, wherein the semiconductor material of the photocathode target comprises cesium telluride.

16. The method of claim 14, wherein the semiconductor material of the photocathode target comprises gallium arsenide.

17. The method of claim 13, wherein the coherent light has a wavelength in a range of ultraviolet light.

18. The method of claim 13, wherein the coherent light has a wavelength in a range of visible light.

19. The method of claim 11, further comprising automated analysis of the image of the area.

* * * * *